United States Patent
Houser et al.

(10) Patent No.: US 9,364,279 B2
(45) Date of Patent: Jun. 14, 2016

(54) USER FEEDBACK THROUGH HANDPIECE OF SURGICAL INSTRUMENT

(75) Inventors: Kevin L. Houser, Springboro, OH (US); William D. Dannaher, Cincinnati, OH (US); Timothy G. Dietz, Terrace Park, OH (US); Foster B. Stulen, Mason, OH (US); Frederick E. Shelton, IV, Hillsboro, OH (US); David C. Yates, West Chester, OH (US); Barry C. Worrell, Centerville, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 231 days.

(21) Appl. No.: 13/276,660

(22) Filed: Oct. 19, 2011

(65) Prior Publication Data
US 2012/0116364 A1    May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 18/12* (2006.01)
*A61B 18/14* (2006.01)
(Continued)

(52) U.S. Cl.
CPC ....... *A61B 18/1442* (2013.01); *A61B 17/00234* (2013.01); *A61B 17/2812* (2013.01); *A61B 17/320068* (2013.01); *A61B 17/320092* (2013.01); *A61B 18/00* (2013.01); *A61B 18/04* (2013.01); *A61B 18/12* (2013.01); *A61B 18/14* (2013.01); *A61B 18/1445* (2013.01);
(Continued)

(58) Field of Classification Search
CPC ................. A61B 2018/00702; A61B 18/1445; A61B 2018/00672; A61B 18/00678; A61B 18/00875
USPC ....................................... 600/587; 606/1, 205
See application file for complete search history.

(56) References Cited

U.S. PATENT DOCUMENTS

| | | |
|---|---|---|
| 1,754,806 A | 4/1930 | Stevenson |
| 3,297,192 A | 1/1967 | Swett |

(Continued)

FOREIGN PATENT DOCUMENTS

| | | |
|---|---|---|
| CN | 101819334 | 9/2010 |
| DE | 102008051866 | 10/2010 |

(Continued)

OTHER PUBLICATIONS

International Search Report and Written Opinion dated Jan. 26, 2012for Application No. PCT/US2011/059212.
(Continued)

*Primary Examiner* — Aaron Roane

(57) ABSTRACT

A surgical instrument includes a handpiece having a user input feature and a user feedback feature. A shaft assembly extends distally from the handpiece. An end effector is disposed at a distal end of the shaft assembly. The end effector includes an active feature responsive to actuation of the user input feature. The active feature is operable to operate on tissue in response to actuation of the user input feature. The user feedback feature is operable to provide feedback to the user that indicates information relating to operation of the end effector. The feedback may include haptic, visual, and/or auditory feedback.

21 Claims, 7 Drawing Sheets

(51) Int. Cl.
  *A61B 17/00* (2006.01)
  *A61B 17/32* (2006.01)
  *A61B 18/00* (2006.01)
  *A61B 18/04* (2006.01)
  *H02J 7/00* (2006.01)
  *A61B 17/28* (2006.01)
  *H01M 2/26* (2006.01)
  *H01M 2/10* (2006.01)
  *A61B 19/00* (2006.01)
  *A61B 17/064* (2006.01)
  *A61B 17/285* (2006.01)
  *A61B 17/29* (2006.01)

(52) U.S. Cl.
  CPC ............ *H02J7/0045* (2013.01); *A61B 17/064* (2013.01); *A61B 17/285* (2013.01); *A61B 18/1206* (2013.01); *A61B 18/1233* (2013.01); *A61B 19/38* (2013.01); *A61B 19/56* (2013.01); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/0019* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H01M 2/10* (2013.01); *H01M 2/26* (2013.01); *Y10T 29/49005* (2015.01); *Y10T 29/49895* (2015.01); *Y10T 29/53913* (2015.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden |
| 4,662,068 A | 5/1987 | Polonsky |
| 4,666,037 A | 5/1987 | Weissman |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. |
| 4,878,493 A | 11/1989 | Paternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,099,537 A | 8/2000 | Sugai et al. |
| 6,165,191 A | 12/2000 | Shibata et al. |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,454,781 B1 * | 9/2002 | Witt et al. ...................... 606/169 |
| 6,500,176 B1 | 12/2002 | Truckai et al. |
| 6,500,188 B2 | 12/2002 | Harper et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,609,414 B2 | 8/2003 | Mayer et al. |
| 6,623,500 B1 | 9/2003 | Cook et al. |
| 6,626,901 B1 | 9/2003 | Treat et al. |
| 6,647,281 B2 | 11/2003 | Morency |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,717,193 B2 | 4/2004 | Olewine et al. |
| 6,730,042 B2 | 5/2004 | Fulton et al. |
| 6,758,855 B2 | 7/2004 | Fulton, III et al. |
| 6,761,698 B2 | 7/2004 | Shibata et al. |
| 6,783,524 B2 | 8/2004 | Anderson et al. |
| 6,815,206 B2 | 11/2004 | Lin et al. |
| 6,821,671 B2 | 11/2004 | Hinton et al. |
| 6,838,862 B2 | 1/2005 | Luu |
| 6,860,880 B2 | 3/2005 | Treat et al. |
| 6,869,435 B2 | 3/2005 | Blake |
| 6,923,807 B2 | 8/2005 | Ryan et al. |
| 6,945,981 B2 | 9/2005 | Donofrio et al. |
| 6,982,696 B1 | 1/2006 | Shahoian |
| 7,031,155 B2 | 4/2006 | Sauciuc et al. |
| 7,077,853 B2 | 7/2006 | Kramer et al. |
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |

(56) References Cited

U.S. PATENT DOCUMENTS

| | | | |
|---|---|---|---|
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Kitahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,083,120 B2 | 12/2011 | Shelton et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 * | 7/2012 | Grant et al. ........................ 606/1 |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,550,106 B2 | 10/2013 | Hebach et al. |
| 8,564,242 B2 | 10/2013 | Hansford et al. |
| 8,617,077 B2 | 12/2013 | Van Groningen et al. |
| 8,641,629 B2 | 2/2014 | Kurokawa |
| 8,663,112 B2 | 3/2014 | Slayton et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton et al. |
| 2005/0256522 A1 | 11/2005 | Francischelli et al. |
| 2006/0030797 A1 | 2/2006 | Zhou et al. |
| 2006/0079829 A1 | 4/2006 | Fulton et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0078484 A1 | 4/2007 | Talarico et al. |
| 2007/0084742 A1 | 4/2007 | Miller et al. |
| 2007/0103437 A1 | 5/2007 | Rosenberg |
| 2007/0173811 A1 * | 7/2007 | Couture et al. ................. 606/39 |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | DeBoer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |

(56) References Cited

U.S. PATENT DOCUMENTS

| | | |
|---|---|---|
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko et al. |
| 2011/0077514 A1 | 3/2011 | Ulric et al. |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0224668 A1 | 9/2011 | Johnson et al. |
| 2012/0179036 A1 | 7/2012 | Patrick et al. |
| 2012/0265230 A1 | 10/2012 | Yates et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger |

FOREIGN PATENT DOCUMENTS

| | | |
|---|---|---|
| DE | 102009013034 | 10/2010 |
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.

(56) References Cited

OTHER PUBLICATIONS

U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
EP Communication dated Feb. 19, 2014 for Application No. EP 11781972.2
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 7, 2013 for Application No. PCT/US2011/059381.
US Office Action, Non-Final, dated Dec. 6, 2013 for U.S. Appl. No. 13/151,471.
US Office Action, Non-Final, dated Mar. 28, 2014 for U.S. Appl. No. 13/151,471.
US Office Action, Notice of Allowance, dated Aug. 19, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Final, dated Nov. 21, 2013 for U.S. Appl. No. 13/151,498.
US Office Action, Non-Final, dated Mar. 18, 2014 for U.S. Appl. No. 13/151,498.
US Office Action, Notice of Allowance, dated Aug. 6, 2014 for U.S. Appl. No. 13/151,498.
US Office Action, Non-Final, dated Jun. 18, 2014 for U.S. Appl. No. 13/151,503.
US Office Action, Non-Final, dated Nov. 6, 2014 for U.S. Appl. No. 13/151,503.
US Office Action, Non-Final, dated Sep. 26, 2013 for U.S. Appl. No. 13/151,509.
US Office Action, Final, dated Jan. 29, 2014 for U.S. Appl. No. 13/151,509.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Restriction Requirement, dated Jun. 11, 2014 for U.S. Appl. No. 13/151,512.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Final, dated Oct. 25, 2013 for U.S. Appl. No. 13/270,667.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Non-Final, dated Nov. 21, 2013 for U.S. Appl. No. 13/271,352.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Non-Final, dated Feb. 14, 2014 for U.S. Appl. No. 13/274,480.
US Office Action, Final, dated Jul. 17, 2014 for U.S. Appl. No. 13/274,480.
US Office Action, Restriction Requirement, dated Dec. 9, 2013 for U.S. Appl. No. 13/274,496.
US Office Action, Non-Final, dated Feb. 6, 2014 for U.S. Appl. No. 13/274,496.
US Office Action, Final, dated May 15, 2014 for U.S. Appl. No. 13/274,496.
US Office Action, Final, dated Aug. 22, 2014 for U.S. Appl. No. 13/274,496.
US Office Action, Restriction Requirement, dated Mar. 28, 2014 for U.S. Appl. No. 13/274,507.
US Office Action, Non-Final, dated Jun. 19, 2014 for U.S. Appl. No. 13/274,507.
US Office Action, Non-Final, dated Dec. 6, 2013 for U.S. Appl. No. 13/274,516.
US Office Action, Final, dated Jun. 12, 2014 for U.S. Appl. No. 13/274,516.
US Office Action, Non-Final, dated Oct. 8, 2014 for U.S. Appl. No. 13/274,516.
US Office Action, Final, dated Oct. 25, 2013 for U.S. Appl. No. 13/274,540.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Final, dated Nov. 26, 2013 for U.S. Appl. No. 13/274,830.
US Office Action, Non-Final, dated Oct. 22, 2014 for U.S. Appl. No. 13/274,830.
US Office Action, Final, dated Dec. 5, 2013 for U.S. Appl. No. 13/275,495.
US Office Action, Non-Final, dated Jan. 6, 2014 for U.S. Appl. No. 13/275,514.
US Office Action, Non-Final, dated Sep. 9, 2014 for U.S. Appl. No. 13/275,514.
US Office Action, Final, dated Feb. 28, 2014 for U.S. Appl. No. 13/275,547.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Final, dated Mar. 21, 2014 for U.S. Appl. No. 13/276,673.

(56) References Cited

OTHER PUBLICATIONS

US Office Action, Non-Final, dated Aug. 14, 2014 for U.S. Appl. No. 13/276,673.
US Office Action, Notice of Allowance, dated Nov. 12, 2013 for U.S. Appl. No. 13/276,687.
US Office Action, Notice of Allowance, dated Jun. 2, 2014 for U.S. Appl. No. 13/276,687.
US Office Action, Notice of Allowance, dated Sep. 12, 2014 for U.S. Appl. No. 13/276,687.
US Office Action, Final, dated Sep. 27, 2013 for U.S. Appl. No. 13/276,707.
US Office Action, Non Final, dated Aug. 20, 2014 for U.S. Appl. No. 13/276,725.
US Office Action, Final, dated Nov. 8, 2013 for U.S. Appl. No. 13/276,745.
US Office Action, Non-Final, dated Feb. 28, 2014 for U.S. Appl. No. 13/276,745.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
International Search Report dated Jan. 12, 2012 for Application No. PCT/US2011/059226.
International Search Report dated Jan. 26, 2012 for Application No. PCT/US2011/059220.
International Search Report dated Feb. 1, 2012 for Application No. PCT/US2011/059223.
International Search Report dated May 29, 2012 for Application No. PCT/US2011/059358.
International Search Report dated Jul. 6, 2012 for Application No. PCT/US2011/059381.
Office Action Non-Final dated Aug. 6, 2013 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Mar. 13, 2013 for U.S. Appl. No. 13/151,509.
Restriction Requirement dated Jun. 24, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Office Action Final dated Aug. 16, 2013 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
Office Action Non-Final dated Dec. 21, 2012 for U.S. Appl. No. 13/276,673.
Office Action Non-Final date Aug. 19, 2013 for U.S. Appl. No. 13/276,673.
Restriction Requirement dated Feb. 6, 2013 for U.S. Appl. No. 13/276,687.
Office Action Non-Final dated Jun. 12, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Australian First Examination Report dated Jun. 17, 2015 for Application No. AU2011323279.
Chinese First Office Action dated Jul. 1, 2015 for Application No. CN 201180063986.1.
Chinese First Office Action dated Mar. 27, 2015 for Application No. CN 2011800638214.
Chinese First Office Action dated Jan. 29, 2015 for Application No. CN 2011800638159.
Chinese First Office Action dated Mar. 4, 2015 for Application No. CN 201180063595X.
US Office Action, Final, dated Apr. 1, 2015 for U.S. Appl. No. 13/151,481.
US Office Action, Notice of Allowance, dated Jun. 10, 2015 for U.S. Appl. No. 13/151,481.
US Office Action, Final, dated Mar. 13, 2015 for U.S. Appl. No. 13/276,673.
US Office Action, Notice of Allowance, dated Dec. 23, 2014 for U.S. Appl. No. 13/276,687.
Japanese Office Action, Notification of Reasons for Refusal, dated Sep. 29, 2015 for Application No. JP 2013-537871.

* cited by examiner

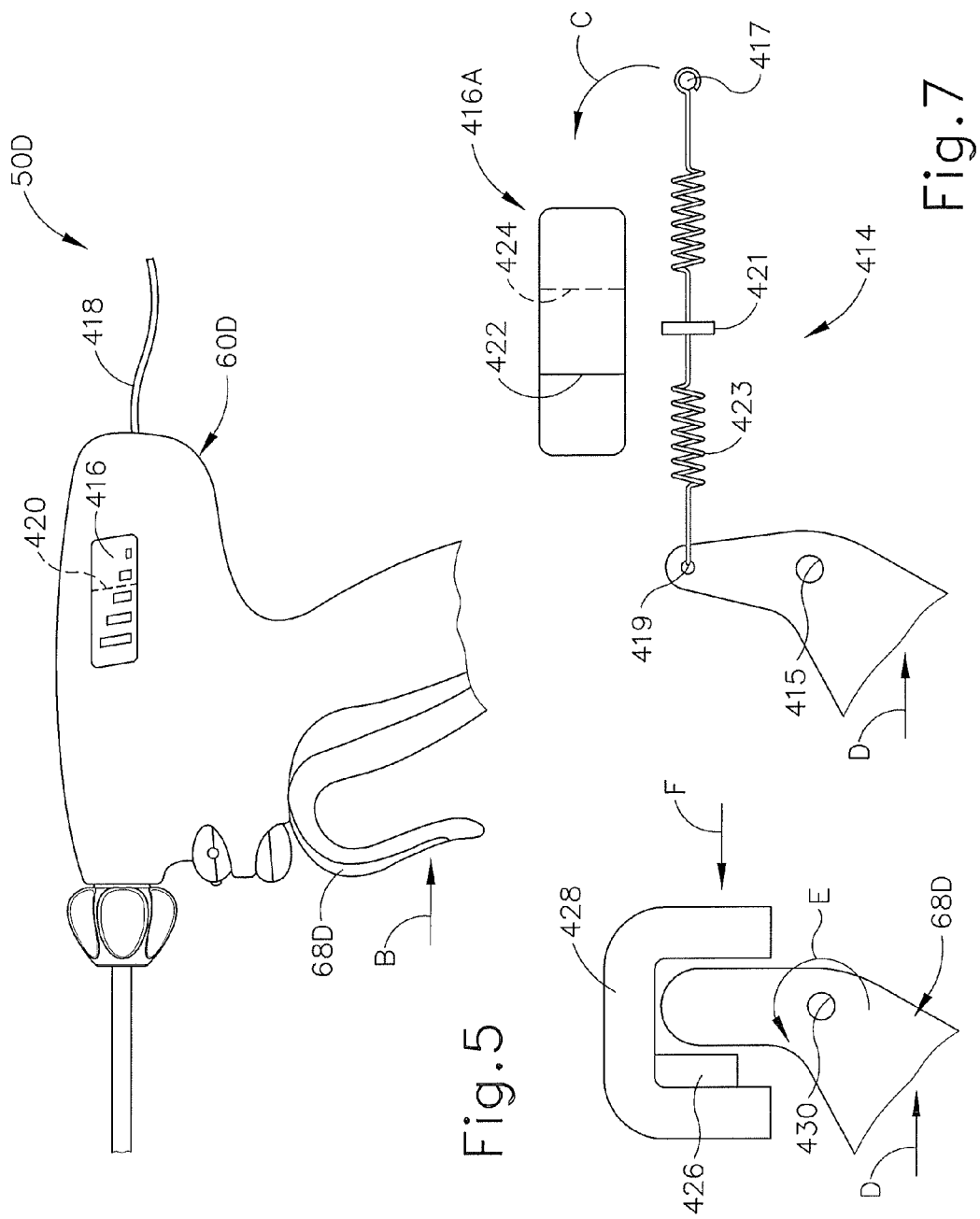

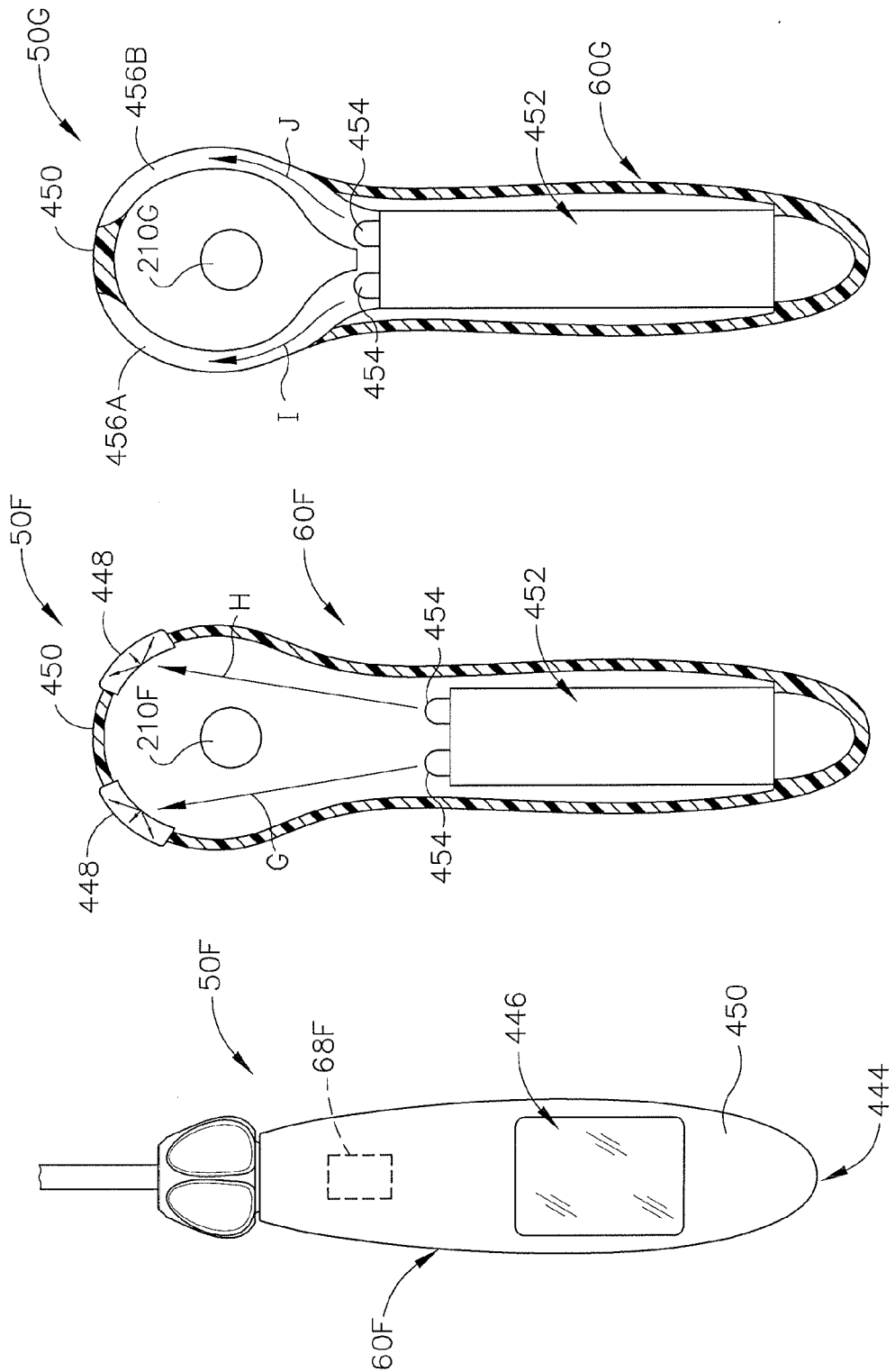

USER FEEDBACK THROUGH HANDPIECE OF SURGICAL INSTRUMENT

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pub. No. 2009/0209990 entitled "Motorized Surgical Cutting and Fastening Instrument Having Handle Based Power Source," published Aug. 20, 2009, now U.S. Pat. No. 8,657,174, issued Feb. 25, 2014, the disclosure of which is incorporated by reference herein; and U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; U.S. Pat. Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5 depicts a side elevational view of an exemplary surgical instrument including a display screen;

FIG. 6 depicts a spring loaded gauge in communication with a trigger of the instrument of FIG. 5;

FIG. 7 depicts a pressure sensor in communication with a trigger of the instrument of FIG. 5;

FIG. 10 depicts a top plan view of an exemplary surgical instrument including a visual indicator screen;

FIG. 11 depicts a cross-sectional view of the instrument of FIG. 10, showing a path for transmission of emitted light from lighting devices to the visual indicator screen;

FIG. 12 depicts a cross-sectional view of the instrument of FIG. 10, showing an alternate path for transmission of emitted light from lighting devices to the visual indicator screen;

Figure 1:
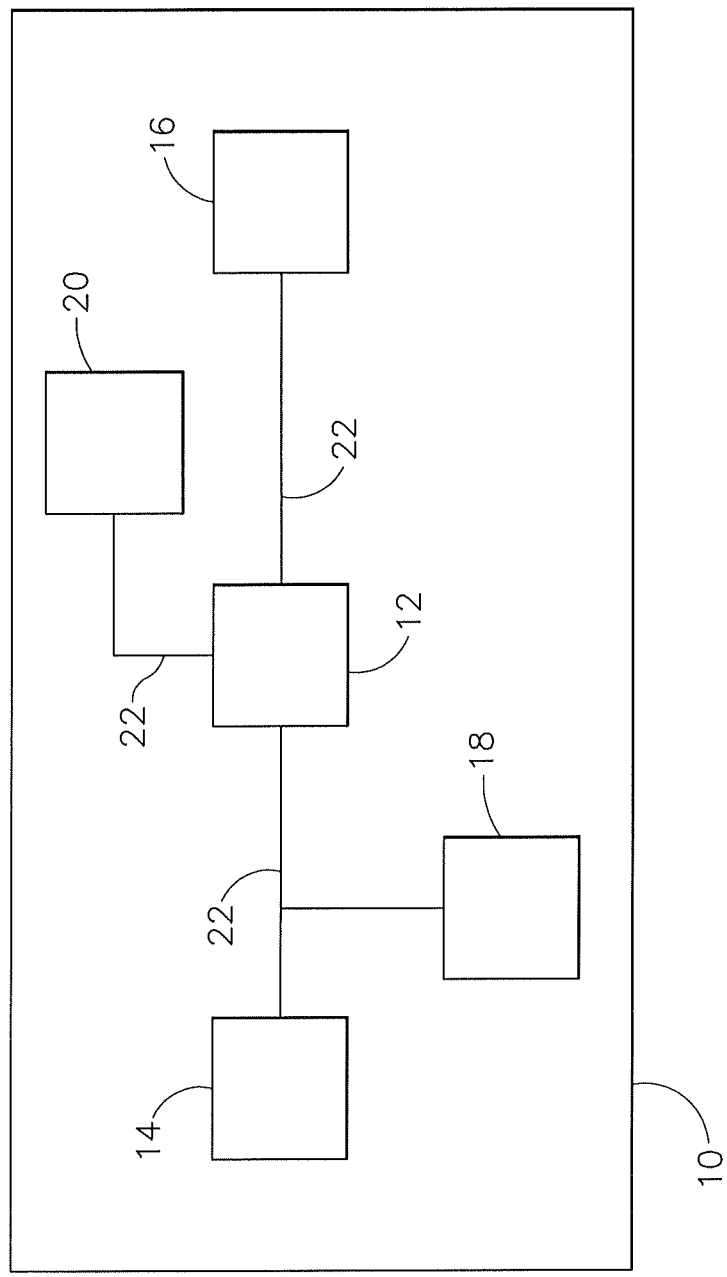
FIG. 1 depicts a schematic view of an exemplary medical device having an internal power source.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Medical Devices for Use with Insertable or Reclaimable Components

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
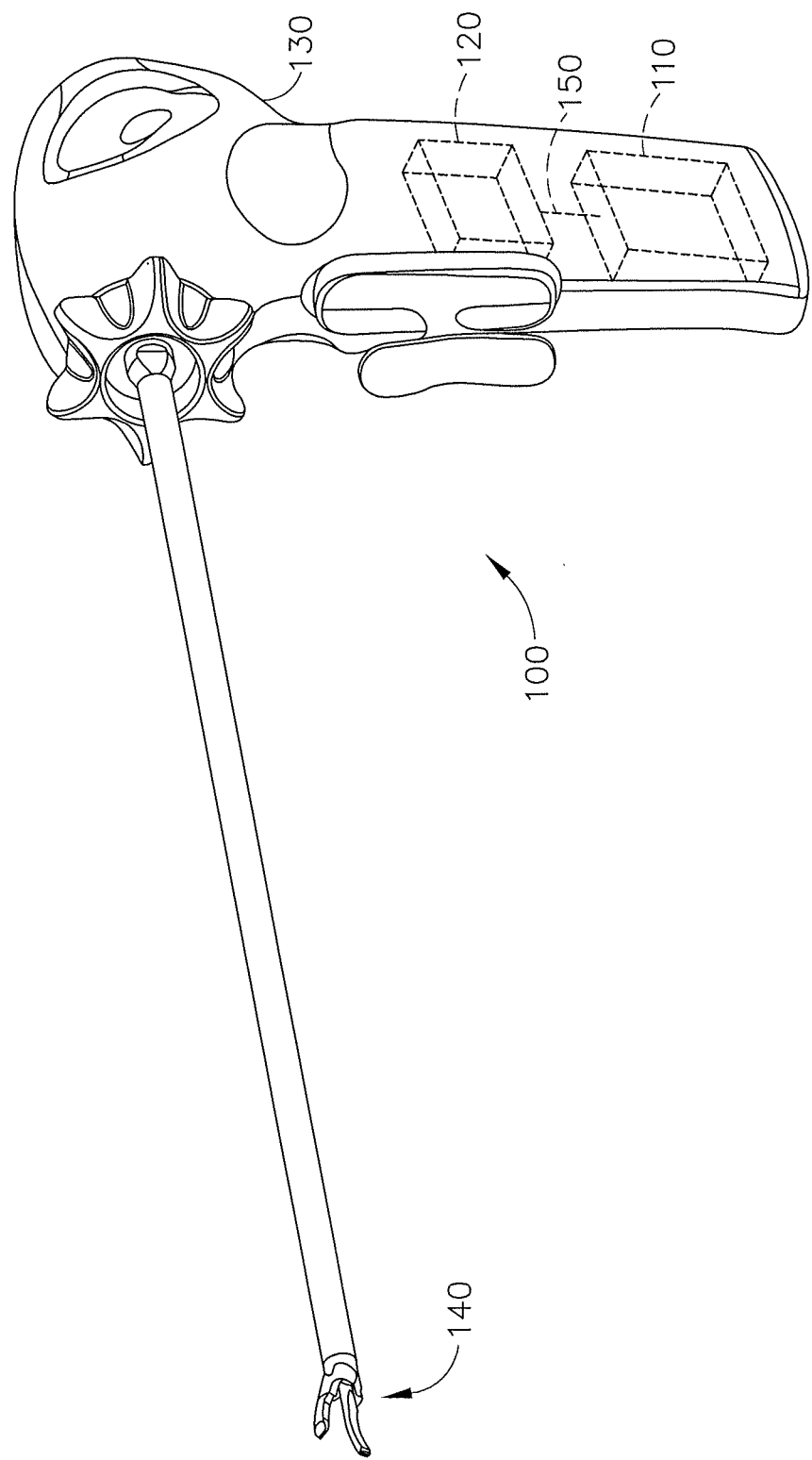
FIG. 2 depicts a perspective view of an exemplary medical device having an internal power source.

FIG. 2 depicts a merely exemplary form that medical device (10) may take. In particular, FIG. 2 shows a medical device (100) comprising a power source (110), a control module (120), a housing (130), end effector (140), and an electrical connection (150). In the present example, power source (110) is located internally within housing (130) of medical device (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130). Power source (110) may also be configured to detach from medical device (100) and decouple from control module (120) or electrical connection (150). As a result, power source (110) may be completely separated from medical device (100) in some versions. As is readily apparent, this may allow the power source (110) to be removed to be recharged or reclaimed for resterilization and reuse, such as in accordance with various teachings herein. After recharging, or after an initial charge, power source (110) may be inserted or reinserted into medical device (100) and secured to housing (130) or internally within housing (130). Of course, medical device (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from medical device (100) for servicing, testing, replacement, or any other purpose as will be apparent to one of ordinary skill in the art in view of the teachings herein. In some versions, power source (110) is external to medical device (100). For instance, power source (110) may be constructed in accordance with at least some of the teachings of U.S. Pat. Pub. No. 2011/0087212, entitled "Surgical Generator for Ultrasonic and Electrosurgical Devices," published Apr. 14, 2011, now U.S. Pat. No. 8,986, 302, issued Mar. 24, 2015, the disclosure of which is incorporated by reference herein.

While certain configurations of an exemplary medical device (100) have been described, various other ways in which medical device (100) may be configured will be apparent to those of ordinary skill in the art in view of the teachings herein. By way of example only, medical devices (10, 100) and/or any other medical device referred to herein may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, now U.S. Pat. No. 9,023,071, issued May 5, 2015, the disclosure of which is incorporated by reference herein; U.S. Pub. No. 2009/0143797, entitled "Cordless Hand-held Ultrasonic Cautery Cutting Device," published Jun. 4, 2009, and issued Apr. 16, 2013 as U.S. Pat. No. 8,419,757, the disclosure of which is incorporated by reference herein; U.S. Pub. No. 2010/0069940 entitled "Ultrasonic Device for Fingertip Control," published Mar. 18, 2010, the disclosure of which is incorporated by reference herein; U.S. Pub. No. 2011/0015660, entitled "Rotating Transducer Mount for Ultrasonic Surgical Instruments," published Jan. 20, 2011, and issued Jun. 11, 2013 as U.S. Pat. No. 8,461,744, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

Of course, housing (130) and medical device (100) may include other configurations. For instance, housing (130) and/or medical device (100) may include a tissue cutting element and one or more elements that transmit bipolar RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201, entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, and published May 10, 2012 as U.S. Pub. No. 2012/0116379, now U.S. Pat. No. 9,161,803, issued Oct. 20, 2015, the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Haptic or Visual Indicators on Ultrasonic Surgical Instrument

Examples described below relate to uses of haptic and/or visual information indicating devices with surgical instruments. It should be understood that the teachings below may be readily incorporated into any of the devices (10, 100) described above and/or any of the devices described in the various references cited herein. Throughout this disclosure, reference numbers utilized with different alphanumeric extensions indicate similar components in different versions of a described reference (i.e., waveguide (210) and waveguide (210F)).

A. Exemplary Haptic Indicators

Figure 3:
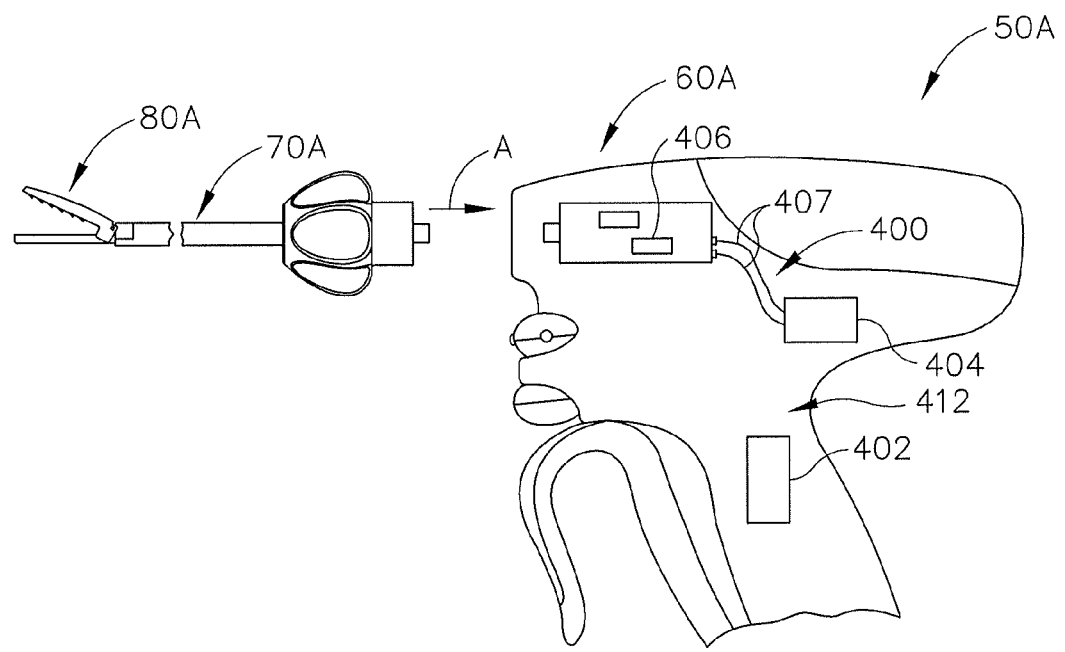
FIG. 3 depicts a side elevational view of an exemplary battery powered surgical instrument having a circuit board and a haptic indicator.

FIG. 3 shows an exemplary surgical instrument (50A), similar to medical device (10, 100) described above, that additionally includes a haptic user feedback system (400). Haptic indicators are currently used in application for cell phones, gaming devices, and other similar applications known to those of ordinary skill in the art. Such devices with haptic indicators provide a tactile sensation to provide a user with feedback. For example, such devices may cause a perceptible continuation or sporadic vibration to a user (to indicate, for example, an incoming call on a cell phone); other devices may provide another type of impulse in reaction to a triggering event or change in status of certain received data or information.

Instrument (50A) includes end effector (80A), multi-piece handle assembly (60A), and elongated transmission assembly (70A). Transmission assembly (70A) may be removably received in the direction of arrow (A) within a distal aperture (not shown) formed in a distal end of multi-piece handle assembly (60A). Instrument (50A) may additionally be a battery-powered device. Battery (402), haptic indicator (404), and circuit board (406) are housed in multi-piece handle assembly (60A).

Haptic indicator (404) may take the form of a vibration generator, for example, that may be constructed and operable in accordance with the teachings of U.S. Patent App. Publ. No. 2011/0152901, entitled "Implantable Port with Vibratory Feedback", published Jun. 23, 2011, now U.S. Pat. No. 8,550, 981, issued Oct. 8, 2013, the disclosure of which is incorporated by reference herein. The vibration generator may comprise a reciprocating or oscillating weight that may be provided by a permanent magnet suspended by a resilient member. Vibration occurs as a selectively energized ring or coil causes the permanent magnet weight to reciprocate or oscillate. Other merely illustrative components and configurations of such a reciprocating weight type of a vibration generator are disclosed in U.S. Pat. No. 7,292,227, entitled "Electronic Device, Vibration Generator, Vibration-Type Reporting Method, and Report Control Method," issued Nov. 6, 2007, the disclosure of which is incorporated by reference herein. Additional exemplary components and configurations that a vibration generator may incorporate are disclosed in U.S. Pat. No. 6,982,696, entitled "Moving Magnet Actuator for Providing Haptic Feedback," issued Jan. 3, 2006, the disclosure of which is incorporated by reference herein; and U.S. Pat. No. 5,800,336, entitled "Advanced Designs of Floating Mass Transducers," issued Sep. 1, 1998, the disclosure of which is incorporated by reference herein. In some versions, the vibration generator may comprise a rotatable weight located eccentric to an axis of rotation and a rotatable by a motor. The rotation of the eccentric weight may cause a vibration. Merely illustrative components and configurations that such a rotating eccentric weight type of a vibration generator may incorporate are also disclosed in U.S. Pat. No. 7,292,227. As another merely illustrative example, a rotating eccentric weight type of a vibration generator may be configured in accordance with the teachings of U.S. Pat. No. 5,107, 155, entitled "Vibrator Motor for Wireless Silent Alerting Device," issued Apr. 21, 1992, the disclosure of which is incorporated by reference herein. By way of example only, the motor may rotate the weight at speeds up to approximately 10,000 rpm or at any other suitable speed.

As another merely illustrative example, a vibration generator may comprise a piezoelectric element. By way of example only, the vibration generator may be configured in accordance with the teachings of U.S. Pat. No. 5,277,694, entitled "Electromechanical Transducer for Implantable Hearing Aids," issued Jan. 11, 1994, the disclosure of which is incorporated by reference herein. As another example, the vibration generator may be configured in accordance with the teachings of U.S. Pat. No. 7,583,564, entitled "Piezoelectric Actuator and Electronic Equipment with Piezoelectric Actuator," issued Sep. 1, 2009, the disclosure of which is incorporated by reference herein. In some other versions, the vibration generator may comprise a piezoelectric element that is contained within a clamshell housing. When the piezoelectric element is excited (e.g., by a transcutaneously applied field, by a signal from a wire that is coupled with the piezoelectric element, etc.), the outward motion of the piezoelectric element pushes outwardly on each half of the surrounding clamshell housing. A vibratory mass may be coupled with one of the clamshell halves, while the other clamshell half may be "grounded" or secured directly to a medical device such as instrument (50A). Thus, if the piezoelectric element pushes upwardly a distance "x" and downwardly a distance "x," the displacement of the vibratory mass relative to the "ground" of instrument (50A) would be "2x."

As yet another merely illustrative example, the vibration generator may comprise a magnetostrictive material. For instance, a magnetostrictive material may be provided as a coil that is wrapped around an inner shaft. The inner shaft may contain the exciting element that acts on the magnetostrictive material. For instance, the inner shaft may be formed by an electromagnet that is selectively activated at a frequency selected to provide a rapid expansion and contraction of the magnetorestrictive material. In particular, when the magnetostrictive material is selectively excited by the inner shaft, the magnetorestrictive material expands and contracts at a rapid rate, producing vibration as it hits upper and lower bounding diaphragms.

As another merely illustrative example, the vibration generator may comprise a lever arm that has a mass at one end and a piezoelectric element under the other end. The piezoelectric element and the fulcrum support of the lever arm may be "grounded" or secured directly to a medical device such as instrument (50A). Other forms of the vibration generator may include one or more solenoids, rotational motors, steppers, etc. In some versions, a vibratory actuator within a vibration generator acts a corporeal vibration/motion energy harvester. For instance, such an energy harvesting actuator may act as an actuator "run in reverse" while it is not actively vibrating instrument (50A), to passively collect energy that can be stored in a battery or capacitor within instrument (50A) for later use when the vibration generator needs to be activated to vibrate. Various ways in which a vibratory actuator (or other component) within the vibration generator or elsewhere can be configured to act as such an energy harvester will be apparent to those of ordinary skill in the art in view of the teachings herein. It should therefore be understood that the vibration generator may be powered by an implanted power source, by an external coil, and/or by an implanted energy harvester, including combinations thereof. Similarly, and regardless of whether an energy harvester is included, other suitable variations, components, features, and configurations of a vibration generator will be apparent to those of ordinary skill in the art in view of the teachings herein.

It should be understood that the choice of the mass of instrument (50A) and the choice of the mass of a moving member in a vibration generator may determine a resonant frequency of the vibration generator. For instance, such masses and resultant resonant frequencies may be selected in accordance with the teachings of Dietz, et al.; "Partially Implantable Vibrating Ossicular Prosthesis"; Transducers '97; International Conference on Solid State Sensors and Actuators; Chicago, Jun. 16-19, 1997; Vol. 1., pp. 433-436, the disclosure of which is incorporated by reference herein. Suitable resonant frequencies for the vibration generator, as well as methods/equations for determining a resonant frequency of a vibration generator, will thus be apparent to those of ordinary skill in the art. In addition, it should be understood that the vibration generator may generate vibrations having any suitable amplitude and frequency. By way of example only, the vibration generated by a vibration generator may have an amplitude of approximately 100 micrometers within a frequency range of approximately 1 Hz and approximately 100 Hz. As another merely illustrative example, the vibration generated by a vibration generator may have an amplitude between approximately 100 micrometers and approximately 10 micrometers within a frequency range of approximately 5 Hz and approximately 100 Hz. As yet another merely illustrative example, the vibration generated by a vibration generator may have an amplitude between approximately 1000 micrometers and approximately 1 micrometer within a frequency range of approximately 10 Hz and approximately 800 Hz. Still other various suitable vibratory frequencies and amplitudes that may be generated by a vibration generator will be apparent to those of ordinary skill in the art in view of the teachings herein.

Circuit board (406) may be a wireless communications board to transmit wireless information about instrument (50A) in a manner apparent to those of ordinary skill in the art in view of the teachings herein. Circuit board (406) may electrically communicate with end effector (80A) via one or more electrical connections and additionally communicates with haptic indicator (404) via one or more electrical connections such as wires (407). In the present example, haptic indicator (404) is attached to pistol grip portion (412) of multi-piece handle assembly (60A). Pistol grip portion (412) encompasses an area where a user's palm will directly contact instrument (50A), such that information may be indicated to the user's palm via haptic contact with pistol grip portion (412) and closely positioned haptic indicator (404). Haptic indicator (404) may be vibrate multi-piece handle assembly (60A) while mechanical and/or electrical energy is applied to instrument (50A). Some forms of information that may be communicated through haptic indicator (404) include, but are not limited to, confirmation of an activation of the end effector, a confirmation of reaching a set threshold amount of resistance measured in ohms applied across operated upon tissue that may additionally serve as a confirmation of the ending stage of severing and sealing tissue via instrument (50A) (or for a surgical instrument receiving RF energy, an indication of tissue state sensed by electrodes positioned in a respective end effector energizing such tissue), confirmation of an attachment of a removable end effector (not shown) within reusable multi-piece handle assembly (60A), an indication of lower battery power within instrument (50A), or other fault indication with respect to instrument (50A), etc. Thus, the user may be informed of important events during the surgical procedure without looking at instrument (50A) to retrieve the information, which might otherwise require the user to look away from the surgical site being operated upon.

Figure 4:
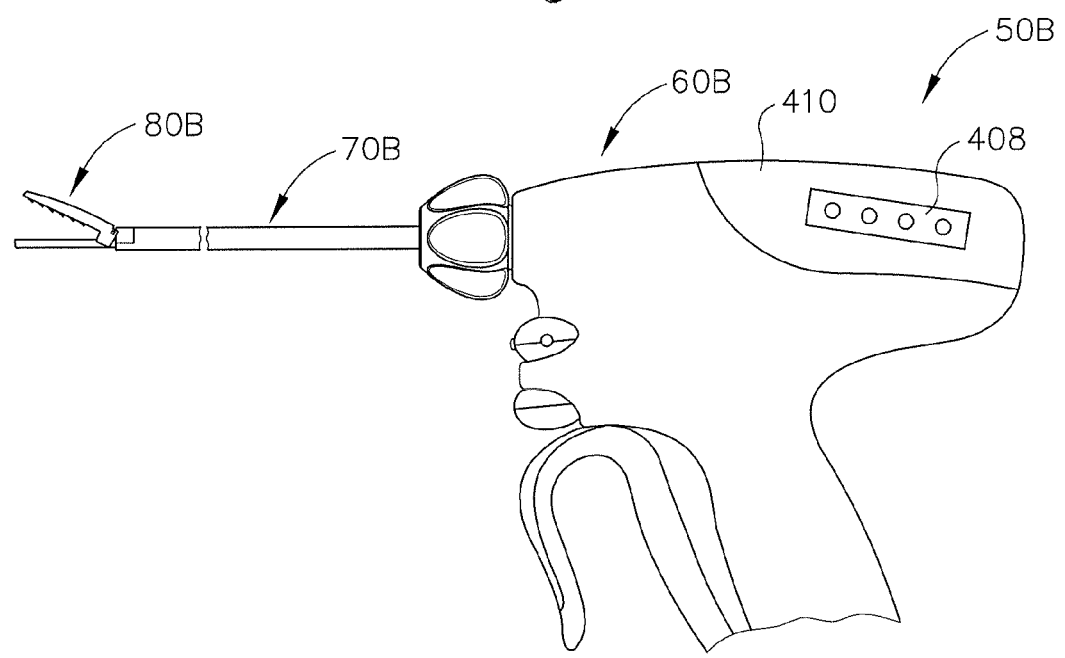
FIG. 4 depicts a side elevational view of an exemplary surgical instrument having a feedback pad.

As shown in FIG. 4, exemplary surgical instrument (50B) may additionally include user feedback pad (408) on an exterior, proximal upper surface (410) for a user to activate and/or operate via the user's fingers, for example. In some such versions, user feedback pad (408) and haptic indicator (404) may form a single unit. FIG. 4 also shows transmission assembly (70B) permanently attached to multi-piece handle assembly (60B), though it should be understood that transmission assembly (70B) may be removable from handle assembly (60B) in some versions. During use of instrument (50B), a user interacts with user feedback pad (408) to obtain information and to input settings for instrument (50B). To ensure that a user has feedback indicating that instrument (50B) has accepted user entered new settings, for example, haptic indicator (404) may provide a tactile feedback such as a vibration. Haptic feedback may provide direct feedback for button pushes and may also provide an indication that instrument (50B) is active while providing an indication of an error codes when device (50B) encounters an error. Additionally or alternatively, feedback to a user indicating that instrument (50B) has accepted new user entered settings or other information may be provided in visual and/or auditory form.

Feedback systems utilized by haptic user feedback system (400) may be, for example, TouchSense® Tactile Feedback Systems and/or TouchSense® Force Feedback Systems provided by Immersion Corporation of San Jose, Calif. (where TouchSense® is a registered trademark of Immersion Corporation). Through use of such haptic technology, it may be possible to provide a haptic click upon completion of an insertion of transmission assembly (70A) into instrument (50A) and/or upon achieving a desirable rotation angle of end effector (80A) to signal to a user that instrument (50A) is properly assembled. For example, a torque sensor may determine when an ultrasonic blade of end effector (80A) and transmission assembly (70A) is properly attached to multi-piece handle assembly (60A) and provide a tactile "click" to a user to indicate such attachment. Also, for surgical instruments requiring one or more electrical connections, a feedback tactile "click" may be sent to a user once a required electrical connection is made.

FIG. 5 shows another exemplary version of ultrasonic surgical instrument (50D), which is similar to medical device (10, 100) described above and includes a force sensor. The force sensor may comprise, for example, pressure sensor (426) of FIG. 6 or spring loaded gauge (414) of FIG. 7, both described further below. The force sensor assists with determining an amount of force a user is applying to trigger (68D) of surgical instrument (50D) in the direction arrow (B). Additionally, instrument (50D) includes a clamping end effector (e.g., like end effector (140) described above, etc.) that clamps upon application of a pressing force on trigger (68D), as described below. Further, instrument (50D) includes a visual and/or haptic indicator to indicate when a clamping force is being applied to tissue via the end effector's response to an actuation of trigger (68D). Visual user feedback panel (416) on surgical instrument (50D) may give a user a graphical representation of such an applied force via utilization of bars or other graphical indications. Additionally or alternatively, a haptic indicator, similar to haptic indicator (404) of surgical instrument (50A), may increase a frequency or level of vibration that is supplied to multi-piece handle assembly (60D). In an alternative version, a circuit board, similar to circuit board (406) of surgical instrument (50A) described above, may communicate information to visual user feedback panel (416) and/or the haptic indicator to respectively allow feedback panel (416) and/or the haptic indicator to indicate to a user the amount of power being supplied to the tissue (such power may be supplied to instrument (50D) via an electrical source, such as cable (418) connected to a generator (not shown)).

In use, a force applied by a user on trigger (68D) that effects clamping on tissue via an end effector of instrument (50D) may have beneficial or detrimental effects on the welding of the clamped tissue. A visual supporting data set, such as via feedback panel (416) described above, may be beneficial to a user, particularly in addition to an optional tonal feedback given to the user. A user may then understand what information instrument (50D) is conveying to the user within minimal disruption from the surgical procedure. Such visual representation of a user load upon instrument (50D) shown via feedback panel (416) compared to a depicted "ideal operation range" or threshold shown on feedback panel (416) via phantom lines (420) would assist a user with understanding what the status of the operated upon tissue might be. Feedback panel (416) may utilize an electrical liquid crystal display ("LCD") type of display or even light-emitted diodes ("LEDs") that light up in discrete steps areas of feedback panel (416). Types of LED displays described herein may also be used in combination with LCD types of displays as will be apparent to those of ordinary skill in the art in view of the teachings herein.

FIG. 6 shows an example of how the clamping force of the end effector of instrument (50D) may be sensed. In particular, FIG. 6 shows pressure sensor (426) built into clamp mechanism (428) of multi-piece handle assembly (60D). Pressure sensor (426) may comprise an electronic pressure sensor, or pressure transducer, converting pressure into an analog electrical signal. Such pressure transducers may utilize force collectors such as a diaphragm to measure strain or deflection due to an applied force over a space. Force collector types may include but not be limited to a piezoresistive strain gauge, capacitive strain gauge, electromagnetic strain gauge, piezoelectric strain gauge, and/or optical strain gauge. Various suitable forms that such gauges may take will be apparent to those of ordinary skill in the art in view of the teachings herein. Similarly, various suitable ways in which such strain gauges may be incorporated into clamp mechanism (428) will be apparent to those of ordinary skill in the art in view of the teachings herein.

It should be understood that sensor (426) may take a variety of additional or alternative forms. For instance, sensor (426) may be operable to measure the acoustic impedance of instrument (50D) (e.g., by comparing current to voltage). In addition or in the alternative, sensor (426) may be operable to measure electrical impedance of tissue. Furthermore, sensor (426) may comprise a displacement measuring device giving feedback on a position of a clamp arm of the end effector (not shown) (e.g., indicating whether the clamp arm is in an open position, closed position, or somewhere between). Sensor (426) may also comprise one or more thermal sensors disposed within the clamp arm of the end effector to register a clamp arm temperature and/or a tissue temperature. Sensor (426) may also comprise a pressure sensor disposed in the clamp arm of the end effector to measure the pressure applied to tissue by the clamp arm and an opposing blade of the end effector. Sensor (426) may additionally be a combination of two or more of the above-described sensors. For example, one or more sensors (426) may be operable to provide information regarding both clamp force as well as clamp arm position. Other suitable forms that sensor (426) may take will be apparent to those of ordinary skill in the art in view of the teachings herein.

Clamp mechanism (428) is coupled with the end effector (not shown) of instrument (50D) such that clamp mechanism (428), along with other components, converts pivotal movement of actuation trigger (68D) into clamping action at the end effector. In particular, clamp mechanism (428) is configured to receive a portion of actuation trigger (68D), which pivots about pin (430). As a user applies force to actuation trigger (68D) in the direction of arrow (D), actuation trigger (68D) rotates about pin (430) in the direction of arrow (E) to apply a force in the direction of arrow (F) against pressure sensor (426). Feedback from pressure sensor (426) may be sent to feedback panel (416) of surgical instrument (50D) to display the feedback information to a user via the LCD display of feedback panel (416). Feedback from pressure sensor (426) may additionally or alternatively be sent through surgical instrument (50D) as a haptic indication, as described above, and/or an audible indication, as described in greater detail below.

FIG. 7 shows another example of how the clamping force of the end effector of instrument (50D) may be sensed. A mechanical indication may occur via spring loaded gauge (414) shown in FIG. 7. Spring loaded gauge (414) of this example includes a gauge (421) positioned between a pair of opposing resilient members such as springs (423), which are connected at a fixed end to fixed point (417) in instrument (50D) and at another end to pin (419) of trigger (68D). Gauge (421) may have any of the configurations noted above for sensor (426) and/or any other suitable configuration. Spring loaded gauge (414) may measure a displacement caused by trigger (68D) and act as a transducer to convert the mechanical displacement into an electrical signal in a manner as apparent to those of ordinary skill in the art in view the teachings herein. Spring loaded gauge (414) may be placed in series with actuation trigger (68D) of surgical instrument (50D) to measure an applied force, shown via solid line (422) in FIG. 7, and transmit the measurement, as shown via arrow (C), to a panel such as feedback panel (416A) for display. For example, a user may press actuation trigger (68D) in the direction of arrow (D) such that trigger (68D) rotates about pin (415). Actuation of trigger (68D) may thus cause an expansion of spring loaded gauge (414), from which a measured of applied force may be retrieved; and release of trigger (68D) may cause spring loaded gauge (414) to return to an original, compressed position. The applied force may then be measured and compared against a preset ideal force, which is indicated as phantom line (424). A "too little force" or a "too much force" condition may thus be indicated to a user. Gauge (414) may additionally or alternatively be a solenoid type gauge. With such a gauge, an increasing force causes an increasing displacement of a core of the solenoid that can be measured in the electrical inputs to the solenoid. Gauge (414) may additionally or alternatively comprise linear variable differential transformers ("LVDTs"). Additionally or alternatively, outputs of instrument (50D) such as blade amplitude and power may be augmented by the information received from feedback features, as described above, as well as other types of indicators such as visual, haptic, and/or auditory indicators.

Figure 8:
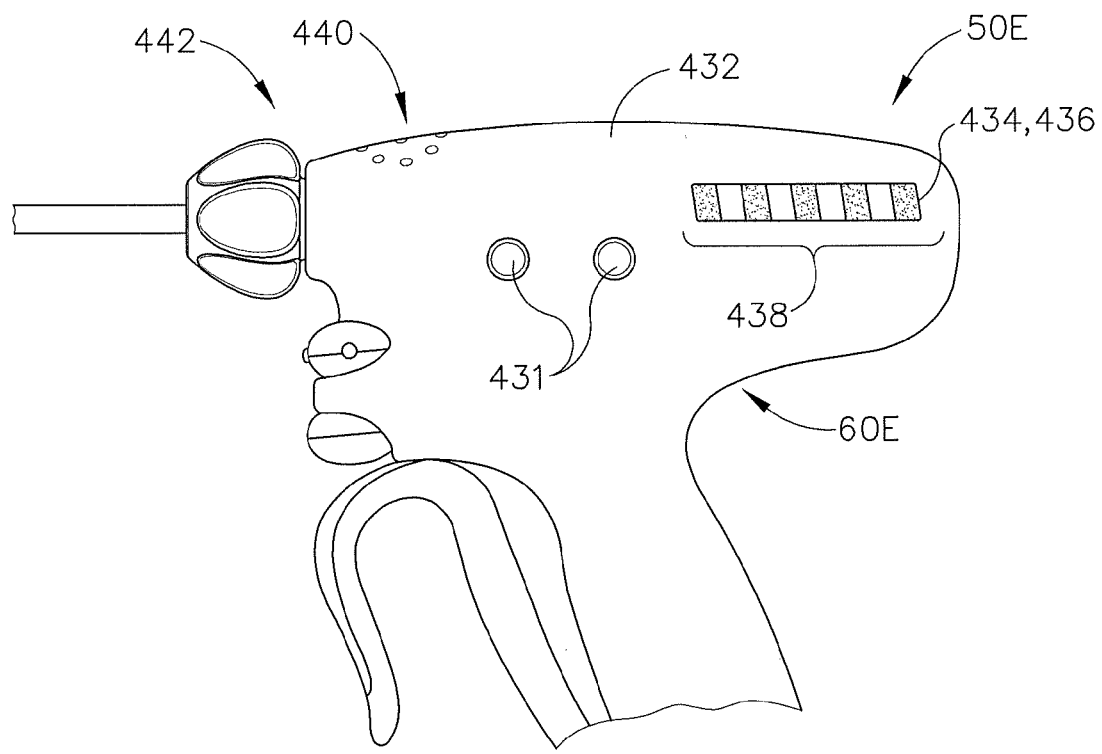
FIG. 8 depicts a side elevational view of an exemplary surgical instrument including a display screen as a visual indicator and speaker holes as an auditory indicator.
Figure 9:
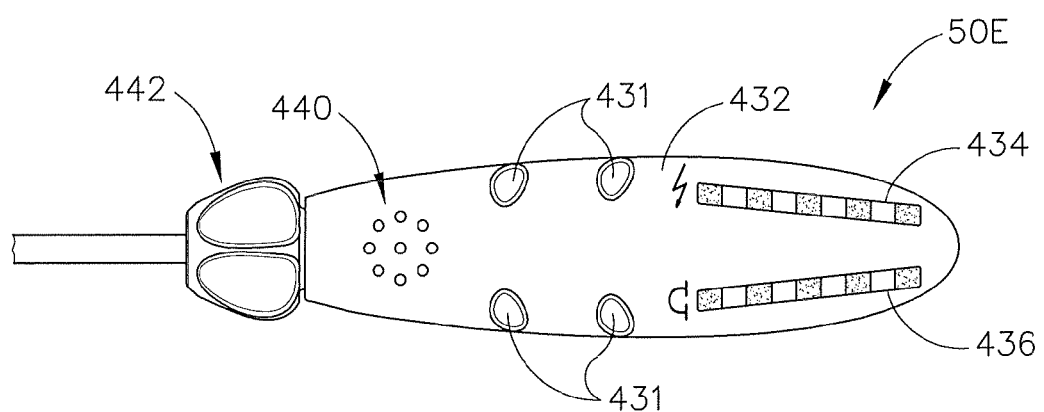
FIG. 9 depicts a plan view of a top surface of the exemplary surgical instrument of FIG. 8.

FIGS. 8-9 show another version of exemplary ultrasonic surgical instrument (50E), which is similar to medical device (10, 100) described above. Surgical instrument (50E) includes hand activation buttons (431) and both auditory and visual feedback features. For example, as shown in FIG. 9, upper surface (432) of multi-piece handle assembly (60E) includes LED indicators (434, 436). LED indicator (434) may provide a visual display bar for indication of an amount of power left in surgical instrument (50E) by, for example, displaying an amount of power left in batteries power surgical instrument (50E). LED indicator (436) may provide a visual display bar for indication of measurements of impedance during use of instrument (50E). For instance, instrument (50E) of this example has an end effector (e.g., similar to end effector (140) described above) with jaws that include sensors. The sensors are used to measure the impedance of tissue being clamped by the jaws. This measured impedance may be monitored to determine the degree to which the tissue is sealed by ultrasonic energy or RF energy, etc. In addition or in the alternative, the measured impedance may be used as a feedback input through a control algorithm to control the delivery of ultrasonic energy or RF energy to the tissue via the jaws. Various suitable ways in which tissue impedance may be measured are described in various references cited herein.

LED indicator (436) as an impedance indicator may change by, for example, lighting up more LED bars or changing a color display as tissue impedance increases. Such a change allows a user to understand that instrument (50E) is approaching a back side of a power curve, or rather, that impedance or resistance to applied voltage has increased, indicating that portions of the operated upon tissue has been sufficiently sealed. Different patterns, such as pattern (438) shown in FIG. 8, may reflect codes relaying a message to a user. For example, if an error occurred when using instrument (50E), a beep pattern from a generator could change from a pre-defined normal pattern reflected by a pattern and number of lit LED bars to a different illuminated non-normal pattern to indicate the error. The normal and non-normal patterns may be set forth in a user guide, for example, to allow a user to interpret the appropriate error message and whether an error is occurring.

With respect to auditory feedback mechanisms, surgical instrument (50E) includes speaker holes (440) on distal end (442) of upper surface (432) of multi-piece handle assembly (60E). A speaker (not shown) disposed below speaker holes (440) will emit sounds to provide audible feedback during activation of instrument (50E). For example, a pattern of audible "beeps" may change upon selection of a minimum or maximum amount of activation power. Or, a pattern or tone may change relative to a measured amount of impedance or power left in the batteries powering surgical instrument (50E), such as projecting a lower pitch or tone as the batteries lose power.

B. Exemplary Visual Indicators

FIGS. 10-13 show an exemplary ultrasonic surgical instrument (50F), similar to medical device (10, 100) described above, that additionally includes a visual indicator to provide visual feedback. FIG. 10 shows proximal end portion (444) of surgical instrument (50F) with a phantom view of projecting trigger (68F). Surgical instrument (50F) includes information display location (446), which may include, for example, a LCD screen including LED lighting imaging to reflect such information from instrument (50F) as described above for other instrument versions.

FIG. 11 shows a cross-section of multi-piece handle assembly (60F) of surgical instrument (50F) including acoustic waveguide (210F). Clear lens (448) is positioned on upper surface (450) of an exterior proximal end portion (444) either as part of information display location (446) or separate from information display location (446). Clear lens (448) may comprise plastic or any other suitable material. Cartridge (452) housed in multi-piece handle assembly (60F) includes electronic module(s) to transmit information and/or batteries to power surgical instrument (50F). One or more projecting light sources (454), which may comprise LEDs, are mounted on an upper surface of cartridge (452). In use, projecting light sources (454) project light through instrument (50F) in the respective directions of arrows (G, H) around acoustic assembly shown by acoustic waveguide (210F) through to clear lens (448), which collects the projected light and transmits the light to enable a user to see the light. Cartridge (452) is removable from multi-piece handle assembly (60F) of surgical instrument (50F) and includes one or more electronics modules. The electronics module(s) of cartridge (452) may control the display functions. Thus, cartridge (452) controls visual feedback to a user as cartridge (452) causes at least one projecting light source (454) to project a light that is seen by the user. The at least one projecting light source (454) is positioned on cartridge (452) such that it is visible to a user through at least one clear plastic lens (448) during use of instrument (50F).

It should be understood that the positioning of cartridge (452) and the use of lens (448) may permit assembly (60F) to be sterilized using gamma sterilization and/or other techniques without harming cartridge (452). In addition or in the alternative, cartridge (452) may be removed to undergo some other form of reprocessing while assembly (60F) is sterilized using gamma sterilization and/or other techniques. In other words, all of the electronic components of instrument (50F) may be contained on cartridge (452), such that the removability of cartridge (452) enables sterilization of assembly (60F) using techniques that might otherwise damage such electronic components.

It should also be understood that transparent bezels, light pipes, and light collectors may be used to assist with projecting light from light sources (454) through lens (448) on upper surface (450) of instrument (50F). For example, FIG. 12 shows an alternate version of exemplary ultrasonic surgical instrument (50G), similar to instrument (50F) described above. However, projecting light sources (454) on cartridge (452) project light in the directions of arrows (I, J) through light tunnels (456A, 456B), which may comprise light pipes or light fibers, for example.

Figure 13:
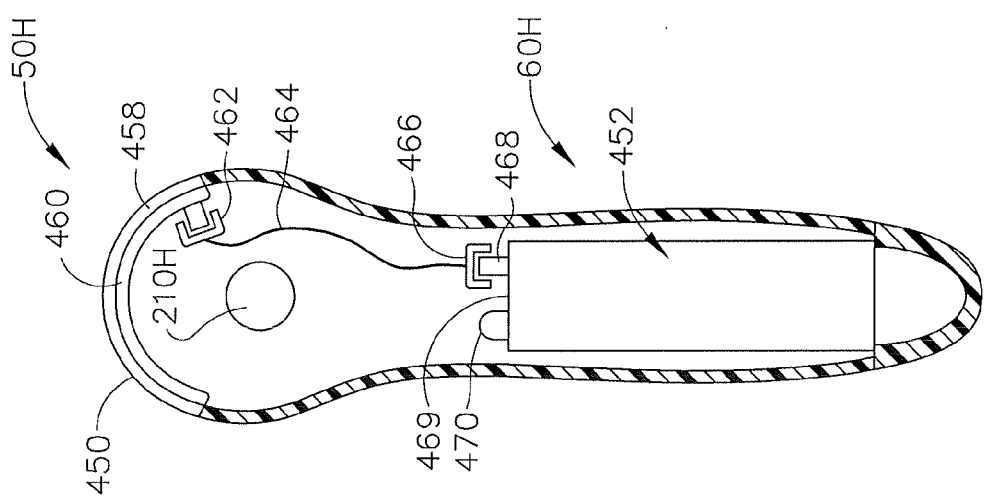
FIG. 13 depicts a cross-sectional view of the instrument of FIG. 10, showing yet another path for transmission of emitted light from lighting devices to the visual indicator screen.

FIG. 13 shows an exemplary ultrasonic surgical instrument (50H), similar to medical device (10, 100) described above, with an exemplary alternative feature to provide visual feedback. Surgical instrument (50H) includes clear bezel (458) positioned on an exterior of upper surface (450) of instrument (50H). Flexible display (460) is disposed within multi-piece handle assembly (60H) or on upper surface (450) below clear bezel (458). Flexible display (460) conforms to the shape of upper surface (450) to better display information such as a display light, text, graphics, etc. through clear bezel (458). While flexible display (460) is shown as disposed beneath clear protective bezel (458), flexible display (460) may alternatively be disposed on the surface of instrument (50H) with a fluid tight electrical connection disposed within multi-piece handle assembly (60H) of instrument (50H). Flexible display (460) is connected to cartridge (452) via a feed-through contact shown as connector (462), discussed below, embedded in the shroud housing of multi-piece handle assembly (60H). Flexible display (460) is operable to display information such as light from light source (470), described below, may be driven by electronic connections from cartridge (452). Flexible display (460) may be a LED, organic LED ("OLED"), electro-chromic, active-matrix OLED ("AMOLED"), or backlight LCD type of display. Information from cartridge (452) is displayed on flexible display (460) for a user to see and use. A touch screen version may be used to enable control of settings such as generator settings through the display.

Connector (462) is in communication with cartridge (452). For example, wires (464) connect connector (462) to electrical connection (466). Electrical connection (466) is mated to a mating electrical connection (468) disposed on top surface (469) of cartridge (452) and electronically communicates with cartridge (452). While electrical connection (466) is shown to be a female connection mated to male mating electrical connection (468), the reverse mating orientation is possible. Light source (470) is disposed on top surface (469) of cartridge (452). Light source (470) may be a light for a back lit LCD or electro-chromic display.

Figure 14:
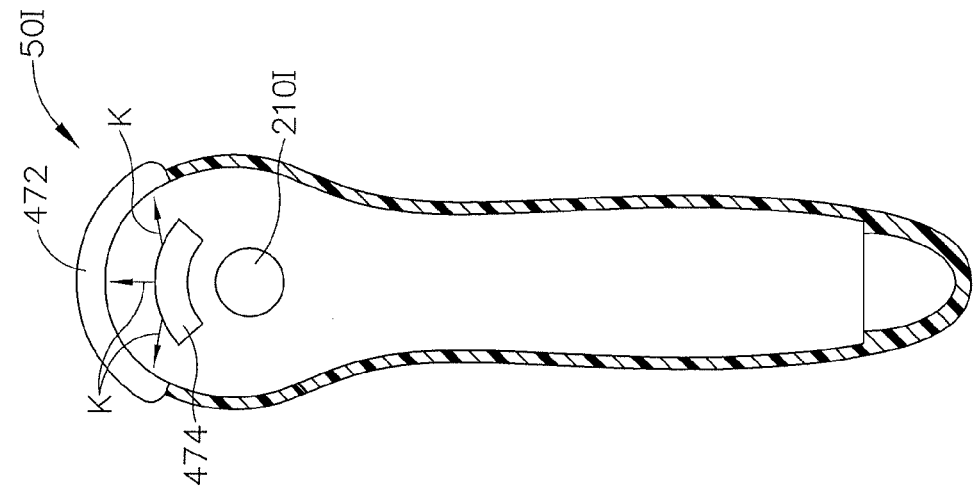
FIG. 14 depicts a cross-sectional view of an alternate version of the exemplary surgical instrument of FIG. 13, in which the flexible display is replaced with a projecting lens.

FIG. 14 shows exemplary surgical instrument (50I), similar to instrument (50H) described above but showing an alternative version. For example, surgical instrument (50I) includes display surface or display screen (472) with projector lens (474) disposed below display screen (472). Projector lens (474) projects information, such as light, for example, onto display screen (472) in the direction of arrows (K). Thus, flexible display (460) is replaced by display screen (472), which provides a surface for projector lens (474) to project information to a user. Projector lens (474) is attached to cartridge (452) by a data cable (not shown) to allow projector lens (474) to project information to a user about instrument (50I).

III. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a handle assembly, wherein the handle assembly comprises a user feedback feature;
   (b) a shaft assembly extending distally from the handle assembly; and
   (c) an end effector disposed at a distal end of the shaft assembly, wherein the end effector is operable to deliver energy from the shaft assembly to a surgical site;
   wherein the user feedback feature is operable to provide feedback to the user, indicating information relating to multiple steps of operation of the end effector including indicating activation of the end effector and indicating whether a threshold impedance value has been reached.

2. The surgical instrument of claim 1, wherein the user feedback feature is operable to provide at least one of a visual, an auditory, or a haptic feedback and is operable to provide information relating to at least one of amplitude of a blade of the end effector or a power level associated with the surgical instrument.

3. The surgical instrument of claim 1, wherein the handle assembly further comprises a user input feature, wherein the end effector includes an active feature responsive to actuation of the user input feature, and wherein the active feature is operable to operate on tissue in response to actuation of the user input feature.

4. The surgical instrument of claim 3, wherein the user feedback feature is operable to provide haptic feedback to a user.

5. The surgical instrument of claim 4, wherein the user feedback feature comprises a haptic motor configured to vibrate in response to a signal of a change in a status of the surgical instrument.

6. The surgical instrument of claim 4, wherein the user input feature comprises a feedback pad configured to receive one or more user inputted setting commands, and wherein the feedback pad and the user feedback feature form one of a single unit or separate units.

7. The surgical instrument of claim 3, wherein the user feedback feature comprises a visual indicator operable to provide visual feedback to a user.

8. The surgical instrument of claim 7, wherein the visual indicator is configured to display information upon a screen disposed on the surgical instrument in response to a signal of a change in a status of the surgical instrument.

9. The surgical instrument of claim 8, wherein the user input feature comprises a trigger, wherein the change in status is associated with a force applied to the trigger.

10. The surgical instrument of claim 8, further comprising a force sensor, wherein the user input feature comprises a trigger, wherein the force sensor is operable to measure force applied through the trigger.

11. The surgical instrument of claim 10, wherein the force sensor comprises a spring loaded gauge in communication with the trigger.

12. The surgical instrument of claim 10, wherein the force sensor is selected from the group consisting of a pressure sensor in communication with the trigger, a pressure sensor in communication with the end effector, an acoustic impedance sensor, a tissue impedance sensor, and a displacement measuring device.

13. The surgical instrument of claim 8, wherein the displayed information comprises at least one of a pattern display or a bar display.

14. The surgical instrument of claim 8, further comprising a removable cartridge disposed in the handle assembly, wherein the screen comprises clear plastic and is disposed on a proximal, upper surface of the handle assembly, wherein the user feedback feature comprises one or more lighting devices in communication with the cartridge, wherein the lighting devices are operable to emit light through the clear plastic screen.

15. The surgical instrument of claim 8, wherein the user feedback feature further comprises a flexible display, wherein the cartridge is in electrical communication with the flexible display, wherein the flexible display is disposed below the clear plastic lens.

16. The surgical instrument of claim 1, wherein the threshold impedance value comprises a tissue impedance value.

17. The surgical instrument of claim 1, wherein the threshold impedance value comprises an acoustic impedance value.

18. A surgical instrument comprising:
(a) a handle assembly, wherein the handle assembly comprises:
   (i) a user input feature,
   (ii) a user feedback feature;
(b) a shaft assembly extending distally from the handle assembly; and
(c) an end effector disposed at a distal end of the shaft assembly, wherein the end effector includes an active feature responsive to actuation of the user input feature, wherein the active feature is operable to operate on tissue in response to actuation of the user input feature, wherein the end effector further includes at least one electrode;
wherein the user feedback feature is operable to provide haptic feedback to the user, indicating information relating to multiple stages of operation of the end effector including indication of activation of the end effector and confirmation of severing and sealing tissue by the end effector.

19. The instrument of claim 18, wherein the user feedback feature is configured to vibrate in response to a level of impedance sensed in tissue engaged by the end effector.

20. The instrument of claim 18, wherein the user feedback feature is further operable to provide an auditory feedback to the user, indicating information relating to operation of the end effector.

21. The instrument of claim 18, wherein the handle assembly comprises a pistol grip, wherein at least part of the user feedback feature is positioned within the pistol grip to transmit haptic feedback to a user through the pistol grip.

* * * * *